US011238756B2

(12) United States Patent
Carroll et al.

(10) Patent No.: US 11,238,756 B2
(45) Date of Patent: Feb. 1, 2022

(54) ANATOMICAL TRAINING AND DEMONSTRATION MODEL FOR NEGATIVE PRESSURE AND INSTILLATION THERAPY

(71) Applicant: KCI Licensing, Inc., San Antonio, TX (US)

(72) Inventors: Christopher A. Carroll, San Antonio, TX (US); Justin Rice, San Antonio, TX (US); Shannon C. Ingram, Bulverde, TX (US); Victor Clarke, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 219 days.

(21) Appl. No.: 16/682,321

(22) Filed: Nov. 13, 2019

(65) Prior Publication Data

US 2020/0160754 A1    May 21, 2020

Related U.S. Application Data

(60) Provisional application No. 62/767,822, filed on Nov. 15, 2018.

(51) Int. Cl.
*G09B 23/34*    (2006.01)
*A61M 1/00*    (2006.01)

(52) U.S. Cl.
CPC ............... *G09B 23/34* (2013.01); *A61M 1/90* (2021.05)

(58) Field of Classification Search
CPC ...... G09B 23/28; G09B 23/30; G09B 23/303; G09B 23/34
See application file for complete search history.

(56) References Cited

U.S. PATENT DOCUMENTS

| 1,355,846 | A | 10/1920 | Rannells |
| 2,547,758 | A | 4/1951 | Keeling |
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |

(Continued)

FOREIGN PATENT DOCUMENTS

| AU | 550575 B2 | 3/1986 |
| AU | 745271 B2 | 3/2002 |

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Kurt Fernstrom

(57) ABSTRACT

A modular wound therapy training device, system, and method of use for the device are provided. The device may include a support tray, an elastic insert, a base within the elastic insert, a recess within the base, a conformable polymer, a dressing and a negative pressure source. The recess may be circumferentially smaller than the base and the conformable polymer may be sized to fit within the recess. The device is preferably sized and shaped to form a system when aligned and assembled with duplicates of the device. A method is provided to apply negative pressure and installation therapy when a negative pressure source is activated through a protective dressing.

30 Claims, 17 Drawing Sheets

(56) References Cited

U.S. PATENT DOCUMENTS

| | | | |
|---|---|---|---|
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,525 B1 * | 6/2001 | Spitalnik | G09B 23/28 434/262 |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,850,454 B2 * | 12/2010 | Toly | G09B 23/285 434/267 |
| 7,862,339 B2 * | 1/2011 | Mulligan | A61M 27/00 434/268 |
| 7,887,330 B2 * | 2/2011 | King | G09B 23/34 434/268 |
| 8,057,236 B2 * | 11/2011 | Miau | G09B 23/28 434/267 |
| 8,635,921 B2 * | 1/2014 | Eckstein | A61M 1/0023 73/865.9 |
| 9,472,121 B2 * | 10/2016 | Pravong | G09B 5/02 |
| 9,974,890 B2 * | 5/2018 | Hudspeth | A61M 1/782 |
| 10,586,470 B2 * | 3/2020 | Parry | G09B 23/303 |
| 10,726,743 B2 * | 7/2020 | Segall | G09B 23/30 |
| 10,803,761 B2 * | 10/2020 | Welch | G06F 3/0325 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2017/0193858 A1 * | 7/2017 | Segall | G09B 23/303 |
| 2020/0349864 A1 * | 11/2020 | Hanna | G09B 23/303 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

(56) References Cited

OTHER PUBLICATIONS

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sep. 3, 1997.
Dattilo, Philip P., Jr., et al.; "Medical Textiles: Application of an Absorbable Barbed Bi-directional Surgical Suture" Journal of Textile and Apparel, Technology and Management, vol. 2, Issue 2, Spring 2002, pp. 1-5.
Kostyuchenok, B.M., et al.; "Vacuum Treatment in the Surgical Management of Purulent Wounds"; Vestnik Khirurgi, Sep. 1986, pp. 18-21 and 6 page English translation thereof.
Davydov, Yu. A., et al.; "Vacuum Therapy in the Treatment of Purulent Lactation Mastitis"; Vestnik Khirurgi, May 14, 1986, pp. 66-70, and 9 page English translation thereof.
Yusupov. Yu.N., et al.; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds" Vestnik Khirugi, Oct. 1988, pp. 48-52, and 8 page English translation thereof.
Davydov, Yu.A., et al.; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al.; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.

\* cited by examiner

ANATOMICAL TRAINING AND DEMONSTRATION MODEL FOR NEGATIVE PRESSURE AND INSTILLATION THERAPY

CROSS-REFERENCE TO RELATED APPLICATIONS

The present application claims the benefit of priority to U.S. Patent Application No. 62/767,822, filed on Nov. 15, 2018, the entire contents of which are incorporated herein by reference.

TECHNICAL FIELD

The invention set forth in the claims relates generally to wound therapy and more particularly, but without limitation, to an anatomical training and demonstration model for negative pressure and instillation therapy.

BACKGROUND

Wound care is a complex field that attempts to manage and heal many types of wounds at various anatomical locations on a patient. To further complicate matters, patients often have difficult and complicated accompanying health issues. Proficiency in wound care can take years of advanced training and exposure to many patients in order to encounter the wide range of clinical situations, therapy options, and potential patient outcomes. A wound treatment training aid can help to simulate various wound types, complexities, and therapy options available to clinicians. A training device may also be used to simulate the dynamic, complicated, and often convoluted healing trajectory as wounds progress. Some common issues in wound therapy include ease of use, efficiency in application and healing, and proper drainage of exudates. To date, there is no art that adequately addresses these challenges. Thus, there is a need for a reusable training aid that allows for wound dressing application practice incorporating components typically used in the field.

SUMMARY

The present disclosure overcomes drawbacks of previously-known art by providing a device, system, and method incorporating a wound model made from elastomeric materials that may simulate the look and feel of skin. In some embodiments, the use of transparent materials allows a view of the simulated dressing-wound bed interface during therapy. The device may include a wound bed and simulated anatomical features imperative to wound therapy setup and application.

The modular wound therapy device may include a support tray. The device may further have an elastic insert sized to fit securely within the tray and the insert further may have a base. The base may have a recess that is circumferentially smaller than the base. The device further may have a conformable polymer sized to fit within the recess. A dressing may be configured to be adhered on top of the elastic insert, and a negative pressure source may be configured to be coupled to the dressing. In some preferred embodiments, the base represents a periwound and the recess represents a wound bed.

In one embodiment, the elastic insert may be made of a transparent rubber having a resiliency and compressibility intended to simulate a human body portion. In certain embodiments, one or more wound bed inserts may be made of, but not limited to, dermasol, pectin, collagen and dehydrated plasma proteins integrated into woven viscous, cellulose membrane, or hydrocolloid. In some embodiments, the wound bed insert further may be made of a plurality of hydrocolloid strips. In one embodiment, the wound bed insert may have an image of a wound on at least one surface.

In certain embodiments, the tray of the device may be transparent. In other embodiments, the tray may have borders colored to depict a patient's skin. Water may be circulated within the device to maintain a desired temperature. The device may include contouring to match specific patient anatomies, including, but not limited to, an intergluteal cleft.

The device further may be operatively coupled to one or more sensors. The one or more sensors may supply readings to a software program indicating pressure levels of a treatment site. A plurality of force sensors may be distributed in an array around the insert to determine applied force.

The device may further have a peristaltic pump that extrudes a liquid from within the base either in or around the wound bed. The device also may have a negative pressure cutout depicted on the insert with the appropriate dimensions to serve as a reference cutout for users. In one embodiment, a heater also may be added to the base to represent body temperature or display redness to demonstrate the impact of a potential treatment. In some embodiments, a clear dermasol object may included (e.g. be packed between the insert and the tray) to simulate tunneling wounds and undermined areas.

A plurality of wound bed inserts may be sized to fit in the recess of the base. In some embodiments, more than one wound bed insert may fit in one recess. In some embodiments, the dressing may be applied about three centimeters from an outer circumferential border of the base.

A wound therapy training system is also provided. The training system may be made up of any of the devices described above aligned to demonstrate multiple wound treatment sites. The plurality of devices may be aligned in series, in parallel, or in other combinations and alignments demonstrating multiple treatment sites.

A method of simulating negative pressure wound therapy is also provided. The method includes assembling the modular device described above and activating the negative pressure source. Alterations of pressure or materials allows the user to recreate a variety of treatment conditions and different types of treatment. In some methods, the device demonstrates wounds on a continuum. The continuum may include, but is not limited to, wounds with non-viable tissue, slough in a wound bed, wounds requiring debridement, and wounds requiring granulation.

In one embodiment of the method, the experiment conditions are 1 cycle with about a 10-minute soak and about 30 minutes of negative pressure wound therapy at about 125 mmHg. In another embodiment, experiment conditions are 10 cycles with about a 20-minute soak and about 45 minutes of negative pressure wound therapy at about 125 mmHg. In yet another embodiment of the method, experiment conditions make up 8 cycles with about a 10-minute soak and 3.5 hours of negative pressure wound therapy at 125 mmHg negative pressure.

A user may create a real-time visualization of wound bed deformation by viewing any side of the device while performing the methods described above. The method further may allow a user to observe macrostrain in a simulated wound bed.

DETAILED DESCRIPTION

A modular training device for negative pressure and installation therapy is provided herein. The modular device illustratively may include a support tray, an elastic insert, a base within the elastic insert, a recess within the base, a conformable polymer, a dressing and a negative pressure source. The recess may be circumferentially smaller than the base and the conformable polymer may be sized to fit within the recess. The dressing may be configured to adhere on top of the elastic insert, and the negative pressure source may be configured to be coupled to the dressing.

Figure 1A:
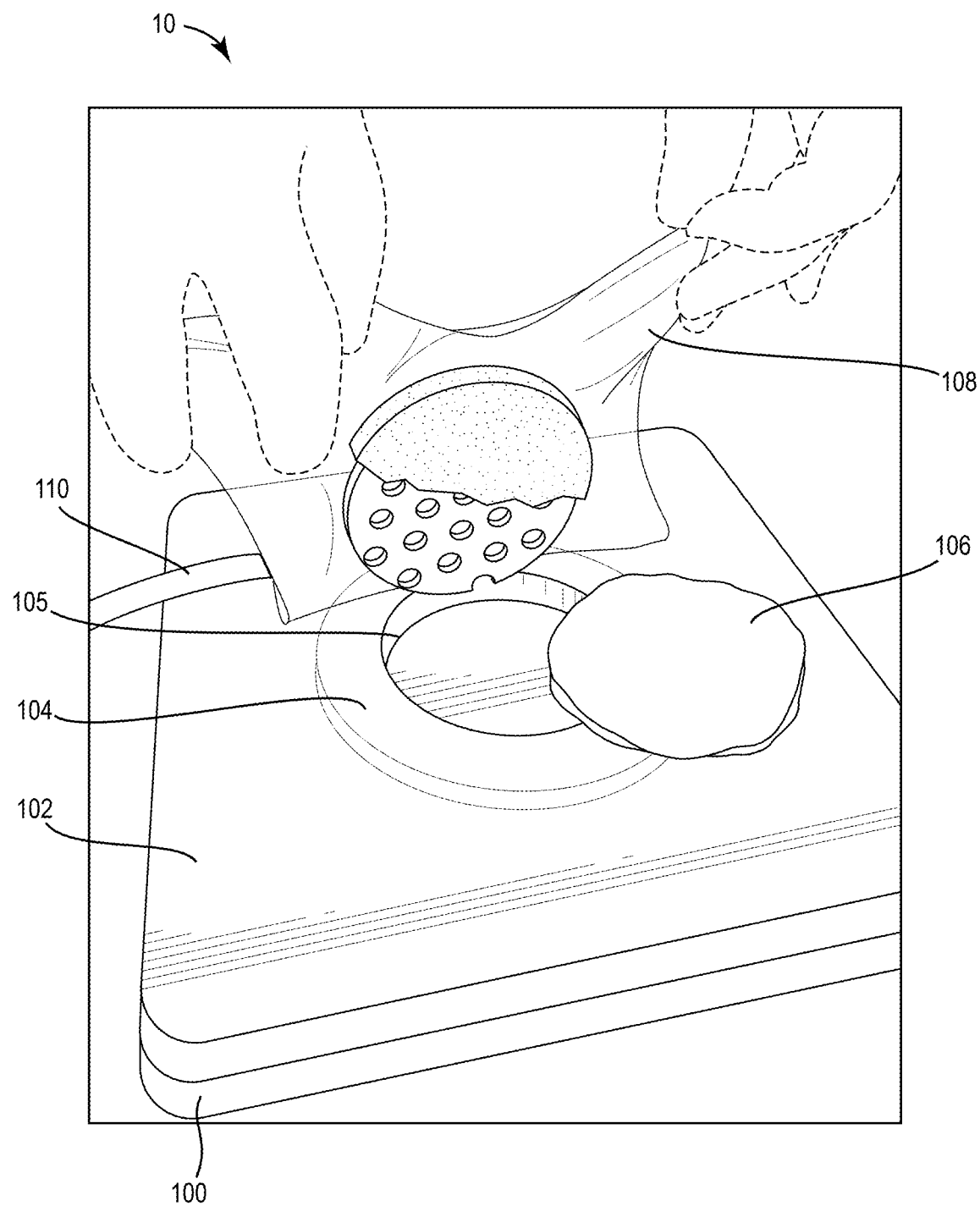
FIG. 1A through FIG. 1G show an exemplary device for modular anatomical training and demonstration model for negative pressure and instillation therapy.
Figure 1B:
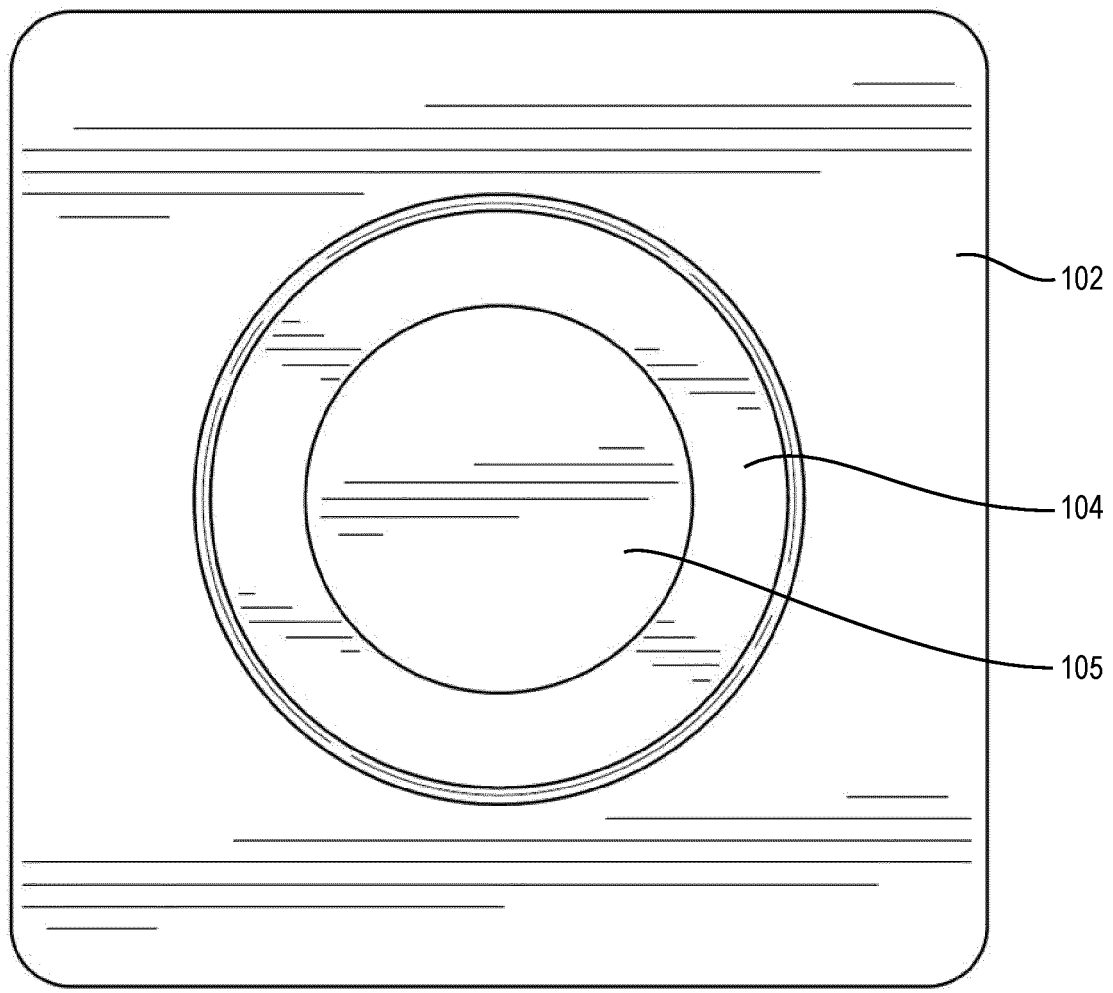
Figure 1C:
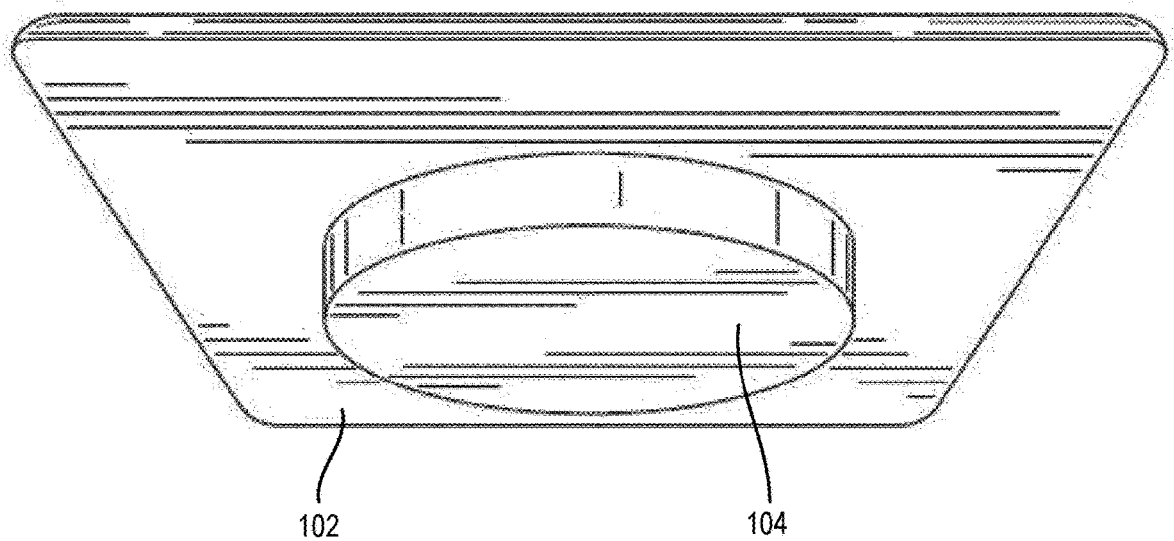
Figure 1D:
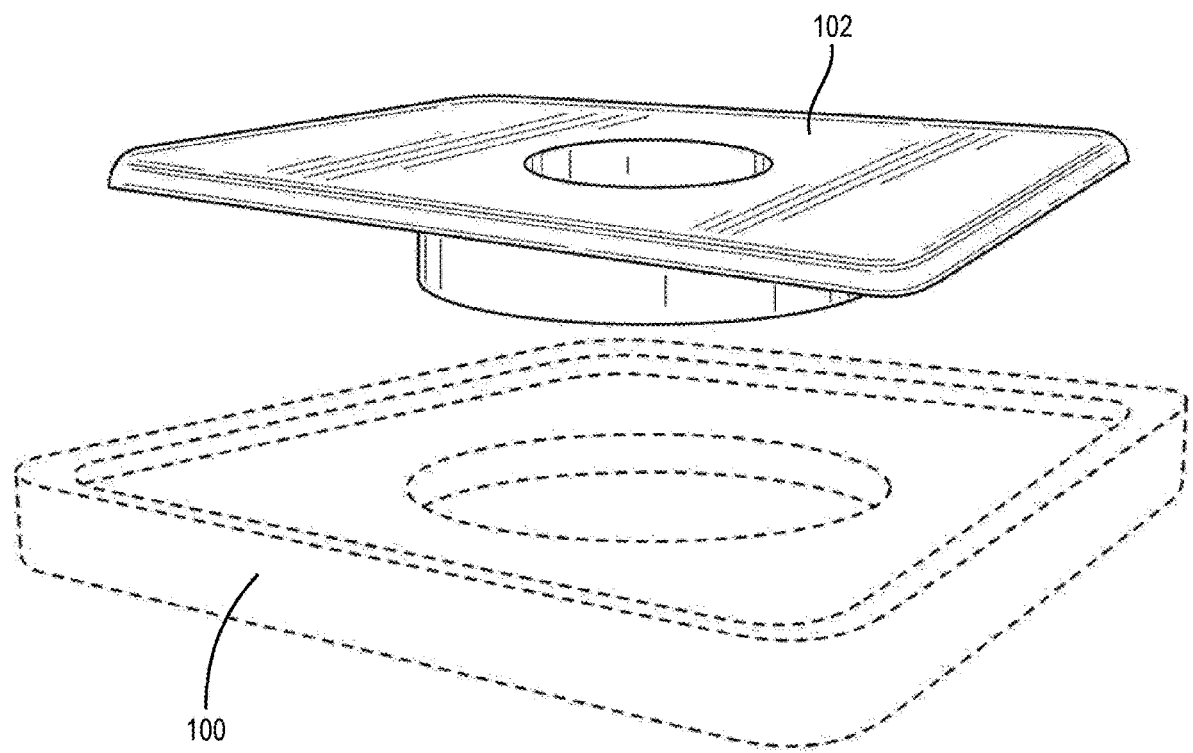
Figure 1E:
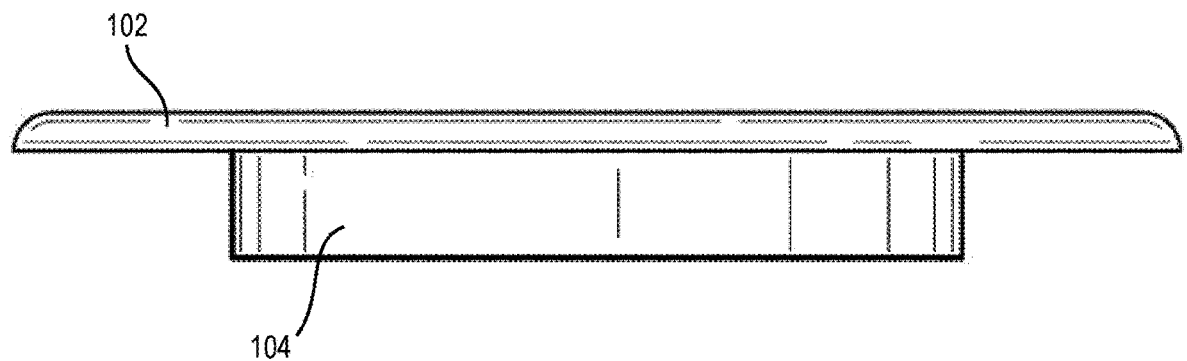
Figure 1F:
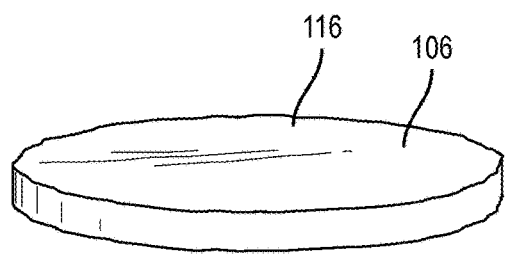
Figure 1G:
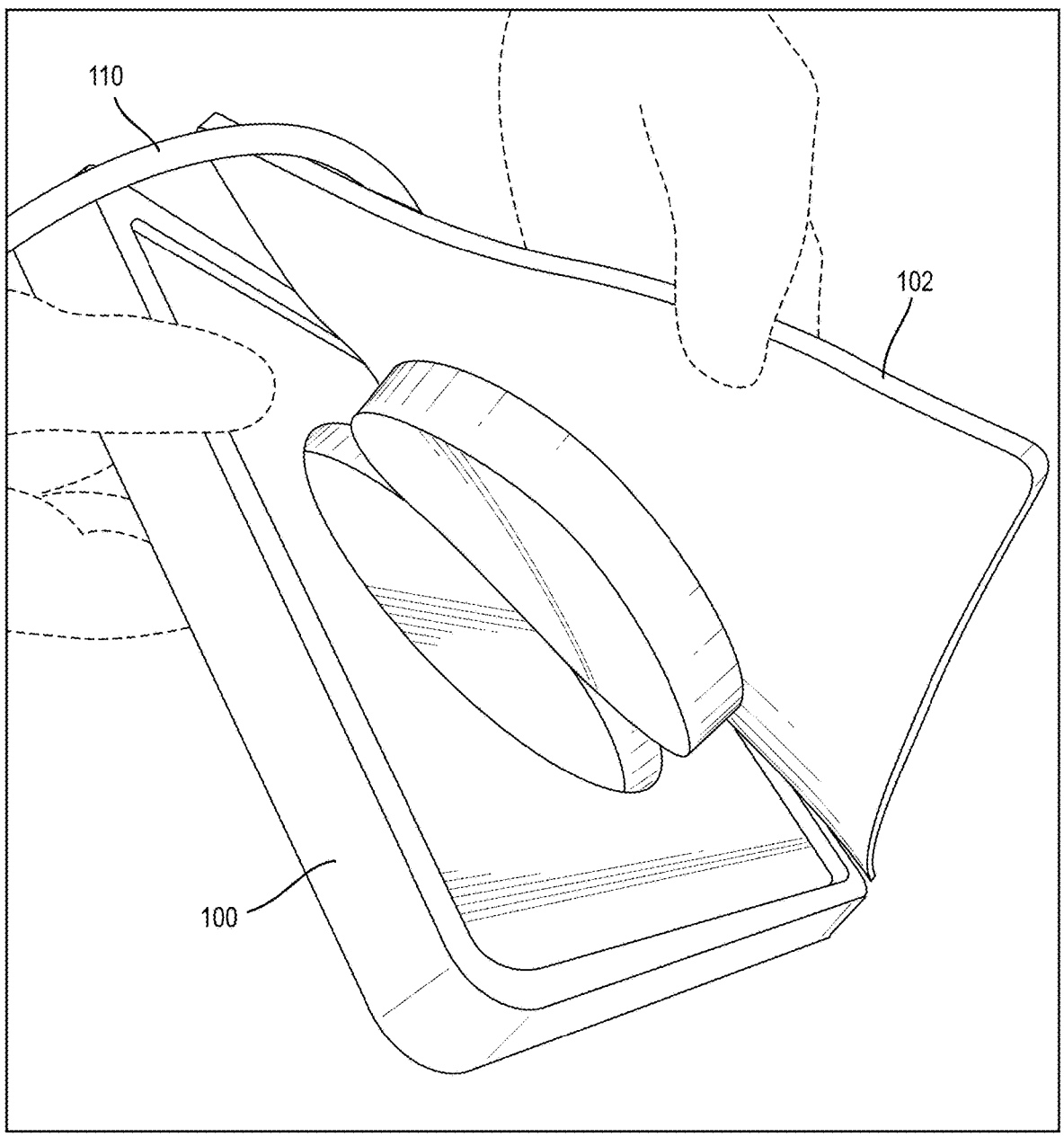

Referring to FIGS. 1A through 1G, an exemplary device used as an anatomical training and demonstration model for negative pressure and instillation therapy in accordance with the principles of the present disclosure is described. FIG. 1A illustrates a front, angled view of modular wound therapy training device 10 comprising support tray 100 and elastic insert 102. Elastic insert 102 may be sized to fit securely within tray 100. Insert 102 is further shown to include a central region generally in the form of a deepened base 104 (e.g. well, bed, holder, etc. and shown to be substantially circular, but may be oval or any suitable shape). Base 104 is intended to simulate a human body part to which a dressing may be applied for training purposes. Base 104 further may have recess 105, where recess 105 is circumferentially smaller than base 104 to present a cup-like recess to hold simulated wound bed materials 106 sized to fit within recess 105, and dressing 108 is configured to adhere on top of elastic insert 102 above base 104. Negative pressure source 110 (as indicated by a tube or lumen leading to a negative pressure source such as a negative pressure pump—not shown) may be configured to be coupled to a top drape portion of dressing 108. FIG. 1B shows a top view of elastic insert 102, wherein base 104 is situated within a central region of elastic insert 102, and recess 105 is situated within base 104. FIG. 1C illustrates a bottom angle view of elastic insert 102, where base 104 is situated in the middle of elastic insert 102, and recess 105 resides in the middle of base 104. The annular region between the outside of base 104 and the outside of recess 105 may have a width of approximately 3 mm and is intended to simulate a periwound region surrounding the wound bed represented by recess 105. FIG. 1D shows an exploded view of tray 100 and elastic insert 102, where elastic insert 102 is sized to fit securely within and couple to tray 100. FIG. 1E shows a side view of elastic insert 102 with base 104 shown in lesser relief below the top planar portion of elastic insert 102. FIG. 1F depicts one embodiment of a simulated wound bed tissue insert (in the form of conformable polymer 106) sized to fit in recess 105. Here, conformable polymer 106 is shown from both a side and front view, separate from recess 105. As shown in FIG. 1G, elastic insert 102 may be formed from a flexible, resilient polymer sized and shaped to couple to negative pressure source 110 and also to fit within tray 100. According to other embodiments, other simulated wound bed materials may be used to present other types of wound bed tissue conditions, such as soft, dry, brittle, etc. For example, in one embodiment, paper or similar materials may be used as a simulated wound bed material to illustrate tears resulting from an undesirable amount of pressure on the wound bed by the trainee during dressing installation. In addition, materials such as hydrocolloid strips or sheets, or ostomy paste may be used to replicate materials routinely needed by caregivers in the treatment of such wounds.

Figure 2:
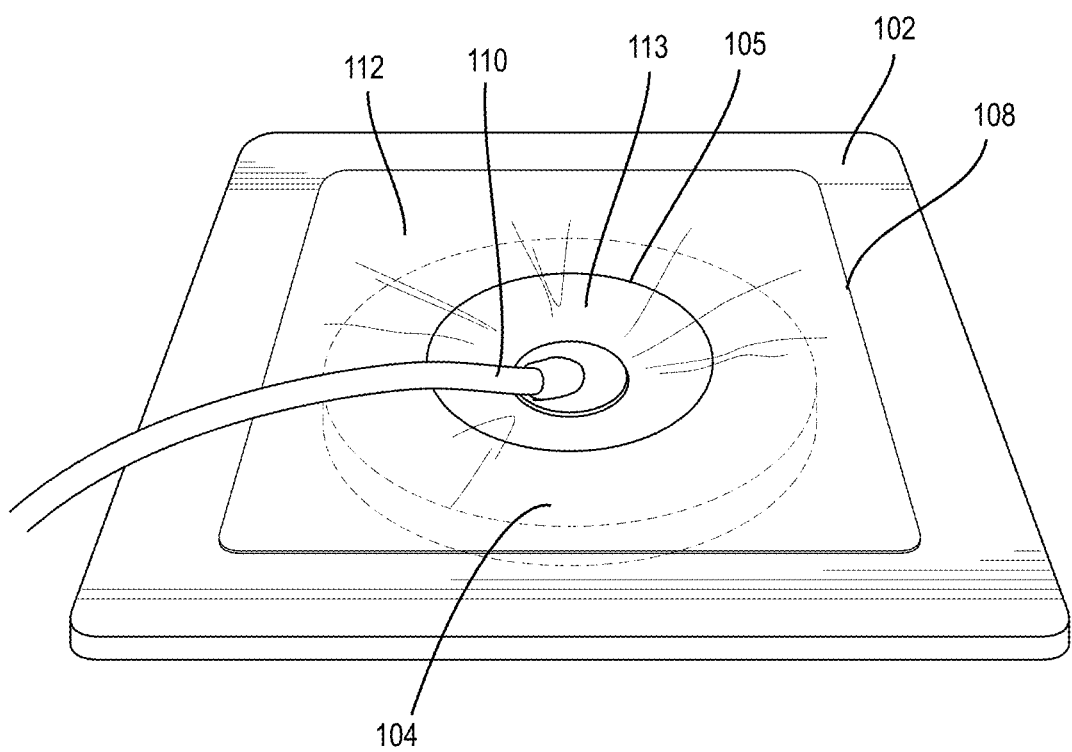
FIG. 2 depicts a top view of the device without the tray wherein the base represents a periwound and the recess represents a wound bed.

As shown in FIG. 2, base 104 may be formed within elastic insert 102 in a manner that represents an outer periwound 112, and recess 105 may be situated within elastic insert 102 to depict the inner wound bed 113.

Figure 3:
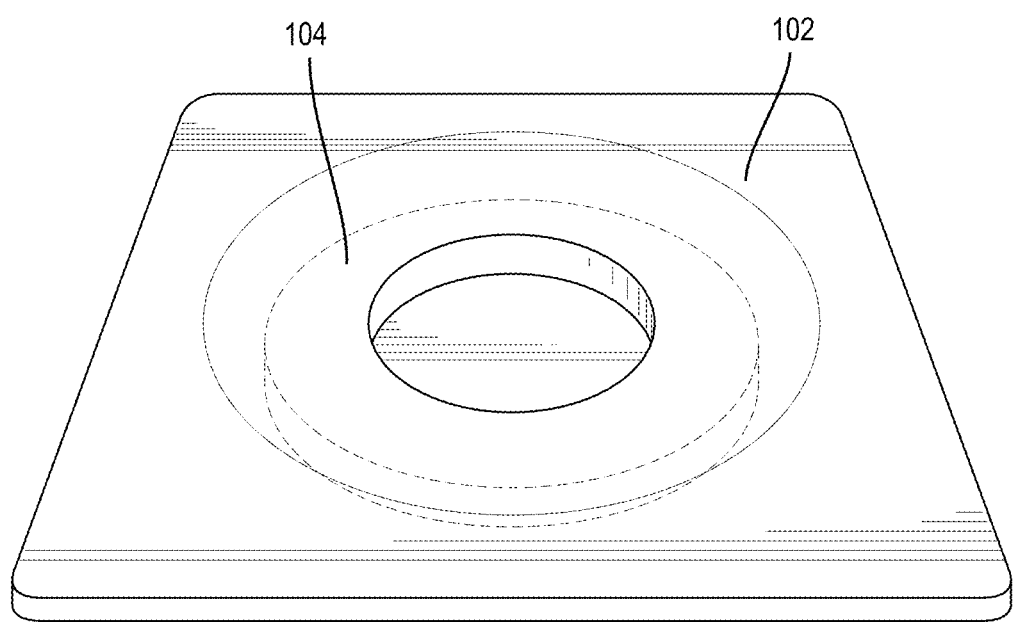
FIG. 3 shows an embodiment wherein the elastic insert is made of a transparent rubber.
Figure 4A:
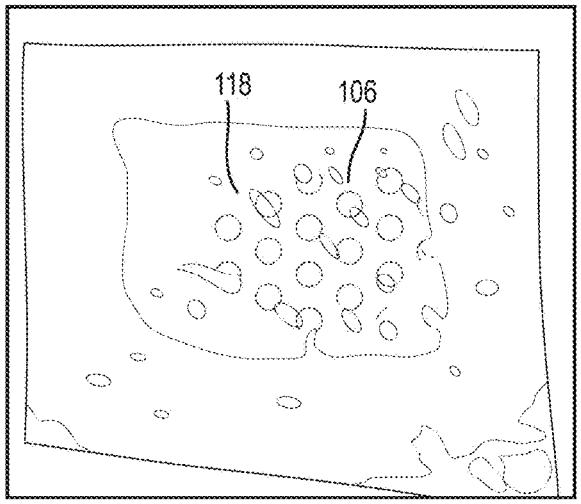
FIG. 4A through FIG. 4D illustrates top views of the conformable polymer comprising four different materials.
Figure 4B:
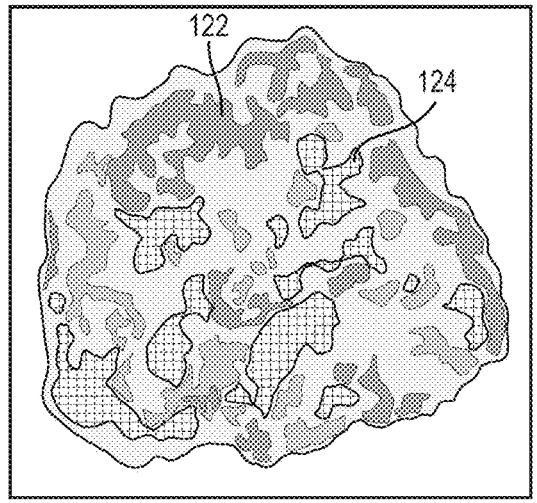
Figure 4C:
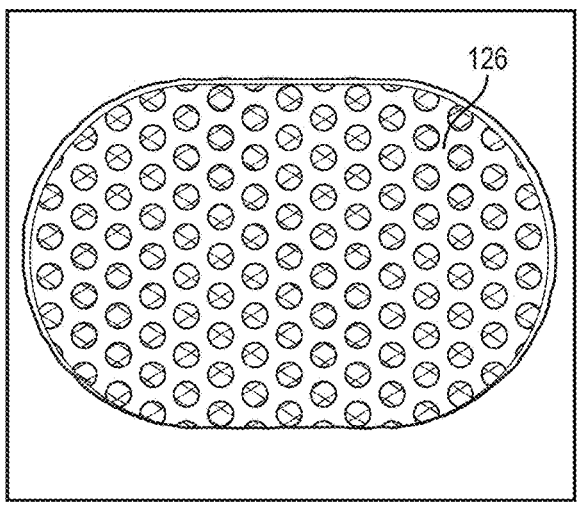
Figure 4D:
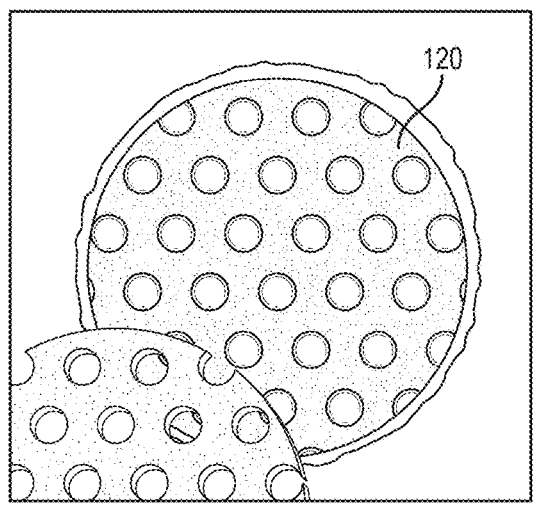

Referring to FIG. 3, elastic insert 102 may be made of substantially transparent, resilient material such as rubber 114 or a semi-transparent rubber that allows for viewing through the top planar surface of elastic insert 102.

FIG. 4 illustrates several different materials that may be used to simulate different tissue models. FIG. 1F, discussed above, depicts dermasol 116 for use as the conformable polymer 106. FIG. 4A shows the use of pectin 118 in conformable polymer 106. FIG. 4B shows dehydrated plasma proteins 122 integrated into woven viscous 124 on conformable polymer 106 to simulate slough and devitalized tissue. The simulated slough may be made of both soluble and insoluble components. FIG. 4C shows cellulose membrane 126, which also may simulate disruption of dried slough. Finally, FIG. 4D illustrates collagen matrix 120 or, alternatively, native collagen demonstrating wound-interface pressure. Conformable polymer 106 may also be made of hydrocolloid or hydrocolloid strips.

Figure 5:
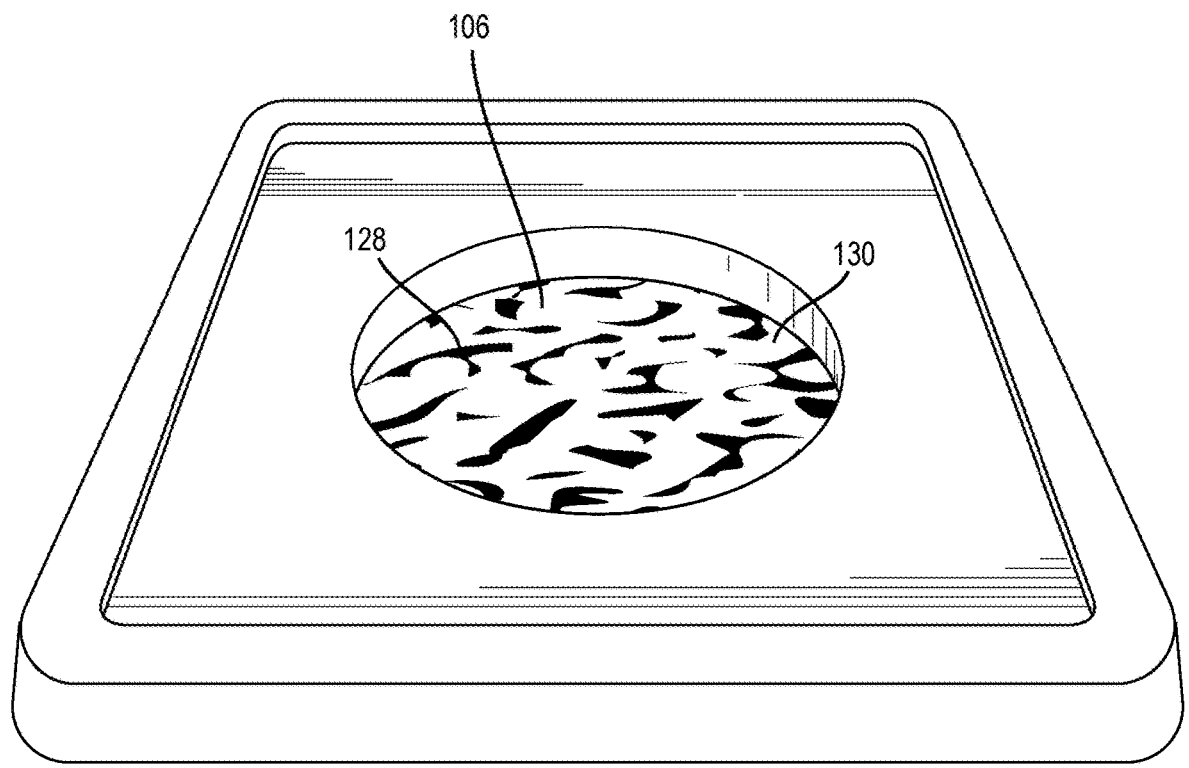
FIG. 5 shows a top view of the device wherein a wound image is displayed on at least one surface of the conformable polymer.

As shown in FIG. 5, conformable polymer 106 may have an image of a wound 128 on at least one surface 130 of conformably polymer 106. The wound image gives clinicians and practitioners using device 10 a more realistic depiction of a wound bed when negative pressure is applied.

Figure 6:
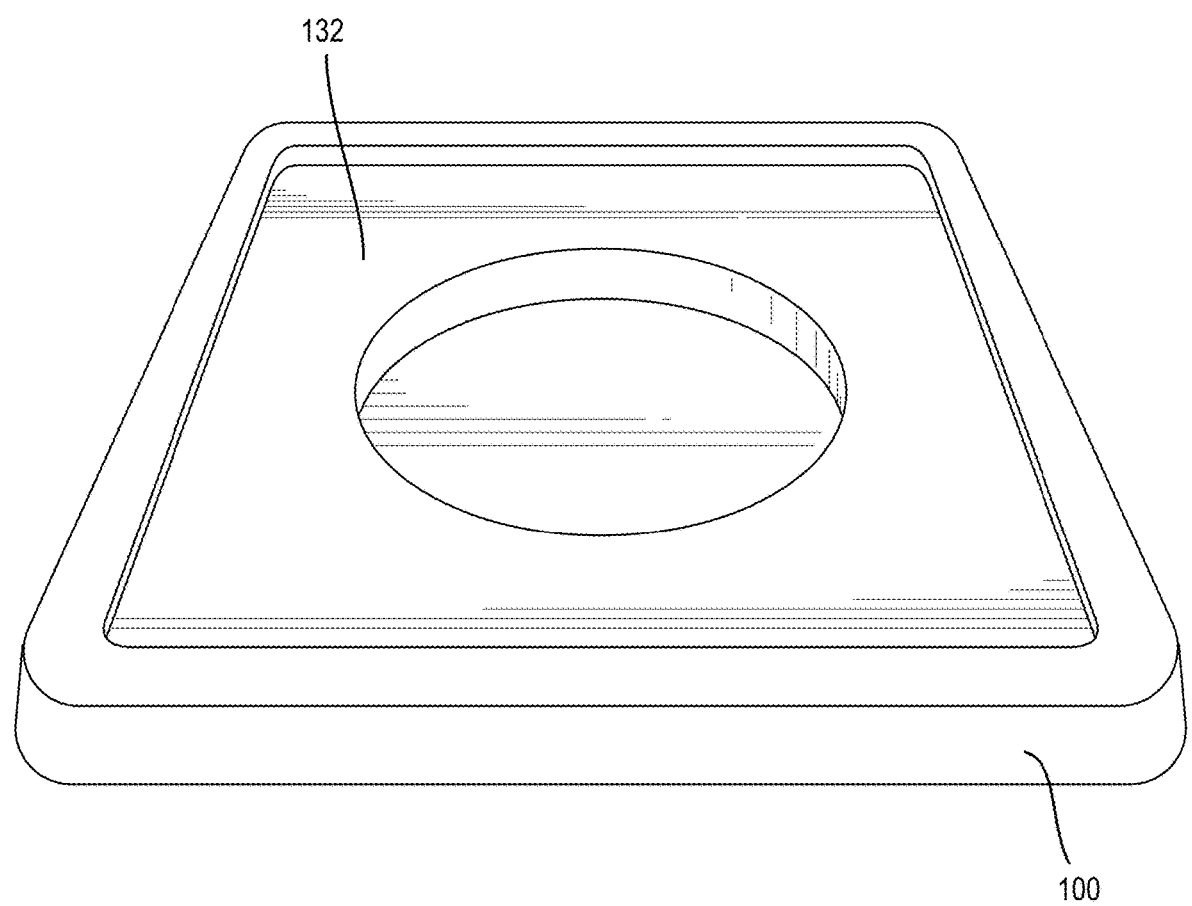
FIG. 6 shows an embodiment of the present disclosure wherein the tray is a transparent plastic.

FIG. 6 shows an embodiment where tray 100 is made from transparent plastic 132. In another embodiment, tray 100 alternatively may have borders colored to depict a patient's skin. Further, tray 100 may also include water circulation passages so that water may be circulated throughout or within device 10 to maintain a desired temperature or to mimic the body heat of a patient.

Figure 7A:
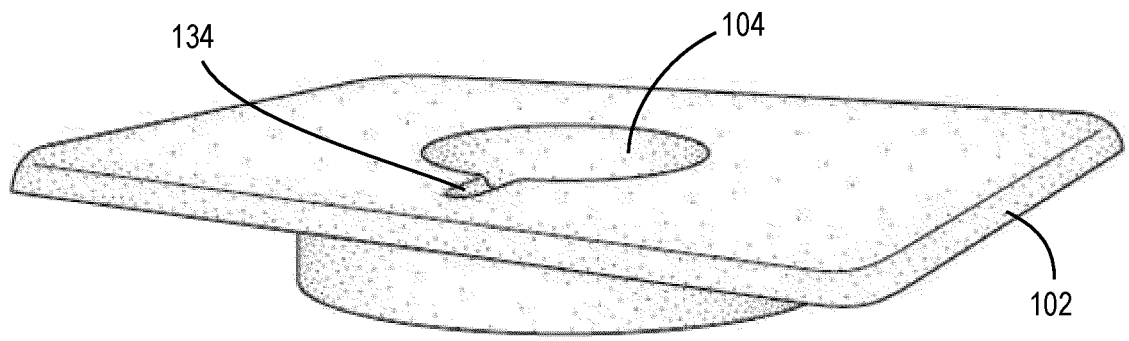
FIG. 7A and FIG. 7B illustrates exemplary embodiments where the device is contoured to match specific anatomies.
Figure 7B:
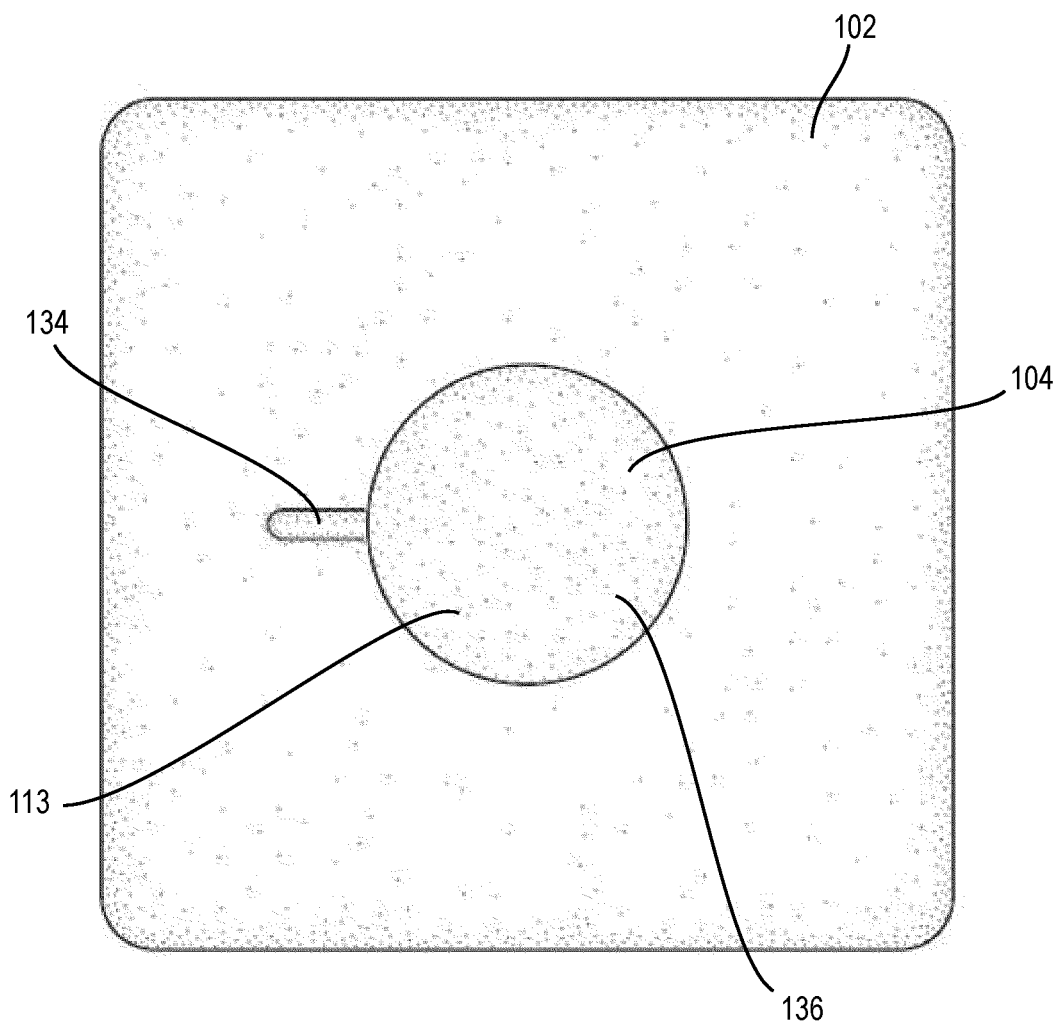

As shown in FIG. 7A-7B, device 10 also may have contouring to match or simulate specific anatomies to which a wound dressing may be applied. FIG. 7A, for example, depicts a forty-five-degree view of a simulated intergluteal cleft 134 formed in the top of base 104. Cleft 134 is intended to present a challenging body contour to which a dressing must be applied with a substantially leak-free seal. FIG. 7B shows a top view of intergluteal cleft 134 extending from base 104. Device 10 further may be operatively coupled to one or more sensors. The one or more sensors may supply readings to an accompanying software program to indicate negative pressure levels of treatment site 136. A plurality of force sensors may be distributed within, around, or on device 10 and insert 102 to determine applied force in an area of the device. The sensors are intended to provide feedback to the trainee regarding the success of the dressing application, by (among others) indicating whether a desired negative pressure can be maintained for a sufficient time period. Device 10 further may have a peristaltic pump designed to extrude liquid from within base 104 either in or around wound bed 113, in order to simulate a wound exudate fluid being drawn from the wound bed during treatment. Such a peristaltic pump (or other suitable pump) may also be used to conduct instillation of fluid to the wound bed, in order to provide the trainee with instillation therapy experience.

Figure 8:
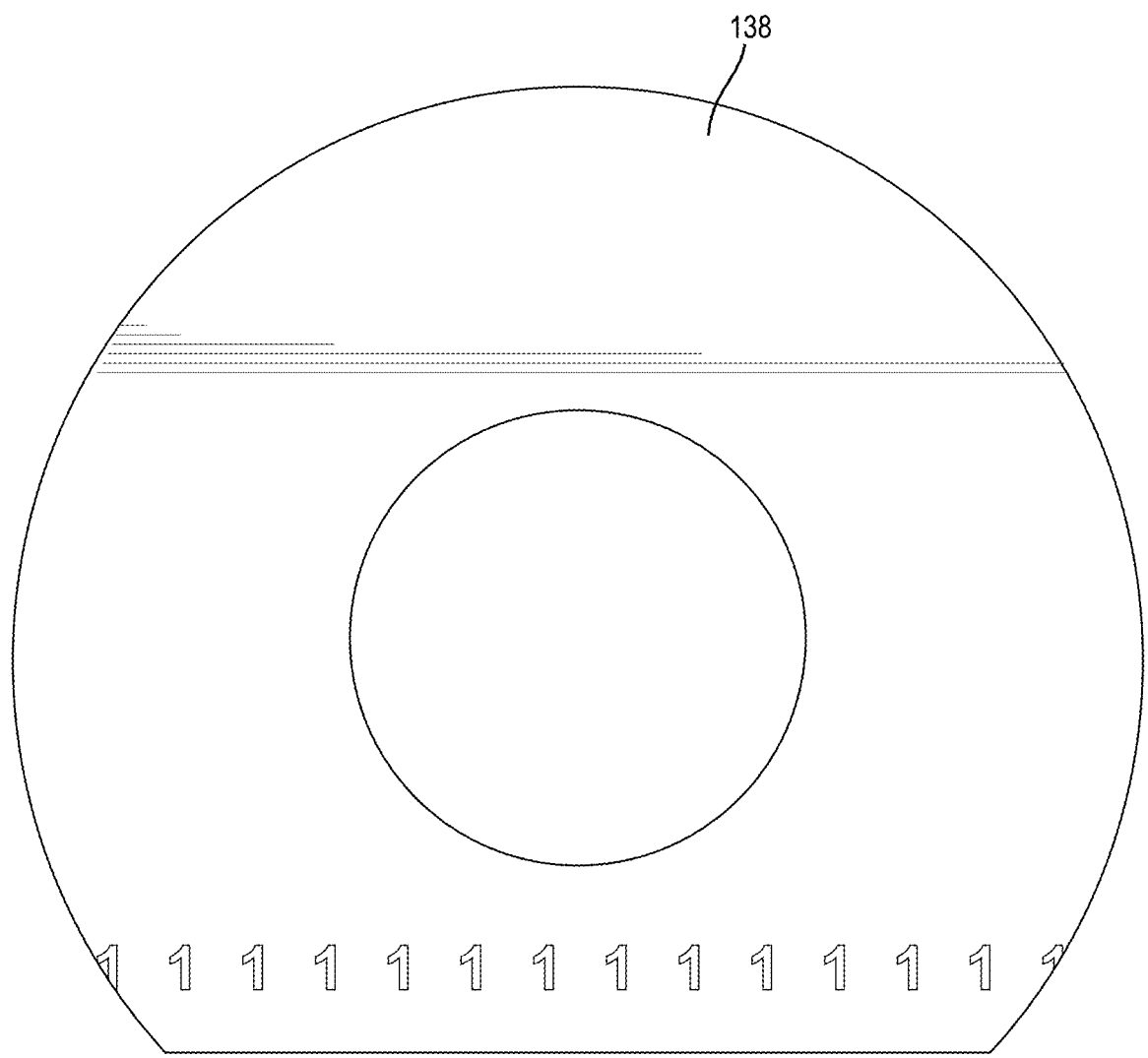
FIG. 8 depicts an exemplary negative pressure cutout with appropriate dimensions to serve as a reference cutout.

FIG. 8 shows an exemplary embodiment of negative pressure cutout template 138, which may be integrated onto insert 102 to serve as a reference for users and clinicians when cutting an opening into a top drape layer of the dressing. The cutout template 138 provides the ideal dimensions of a negative pressure opening to be cut into a top drape layer of dressing 108 for attaching a negative pressure interface (e.g. a flange of a tubing connector, etc.).

Device 10 further may have a heater in base 104 to represent body temperature or inflammation. Device 10 further may display redness, from a heated, electronic, or other source, to demonstrate the impact of a potential treatment or to indicate where a trainee has made a mistake in their use of device 10. In some embodiments, device 10 may also have at least one clear dermasol object packed within a suitable elongated cavity within insert 102 (or between insert 102 and tray 100) to simulate a tunneling wound or an undermined skin healing area.

Figure 9A:
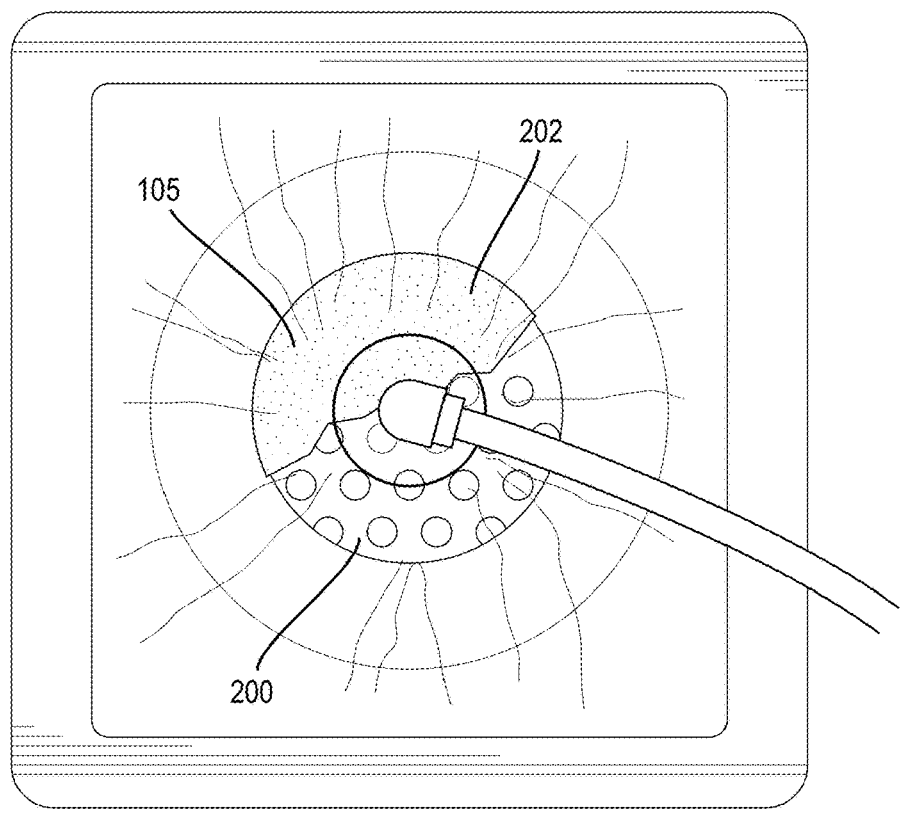
FIG. 9A shows a top view of an alternative embodiment where a plurality of conformable polymers are sized to fit in the recess.
Figure 9B:
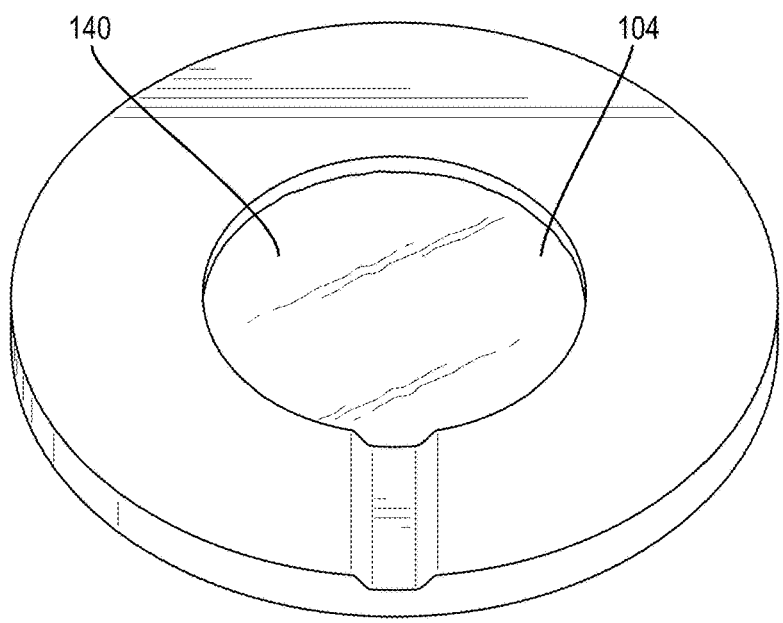
FIG. 9B illustrates an embodiment where the dressing is applied about three centimeters from an outer circumferential border of the base.
Figure 11:
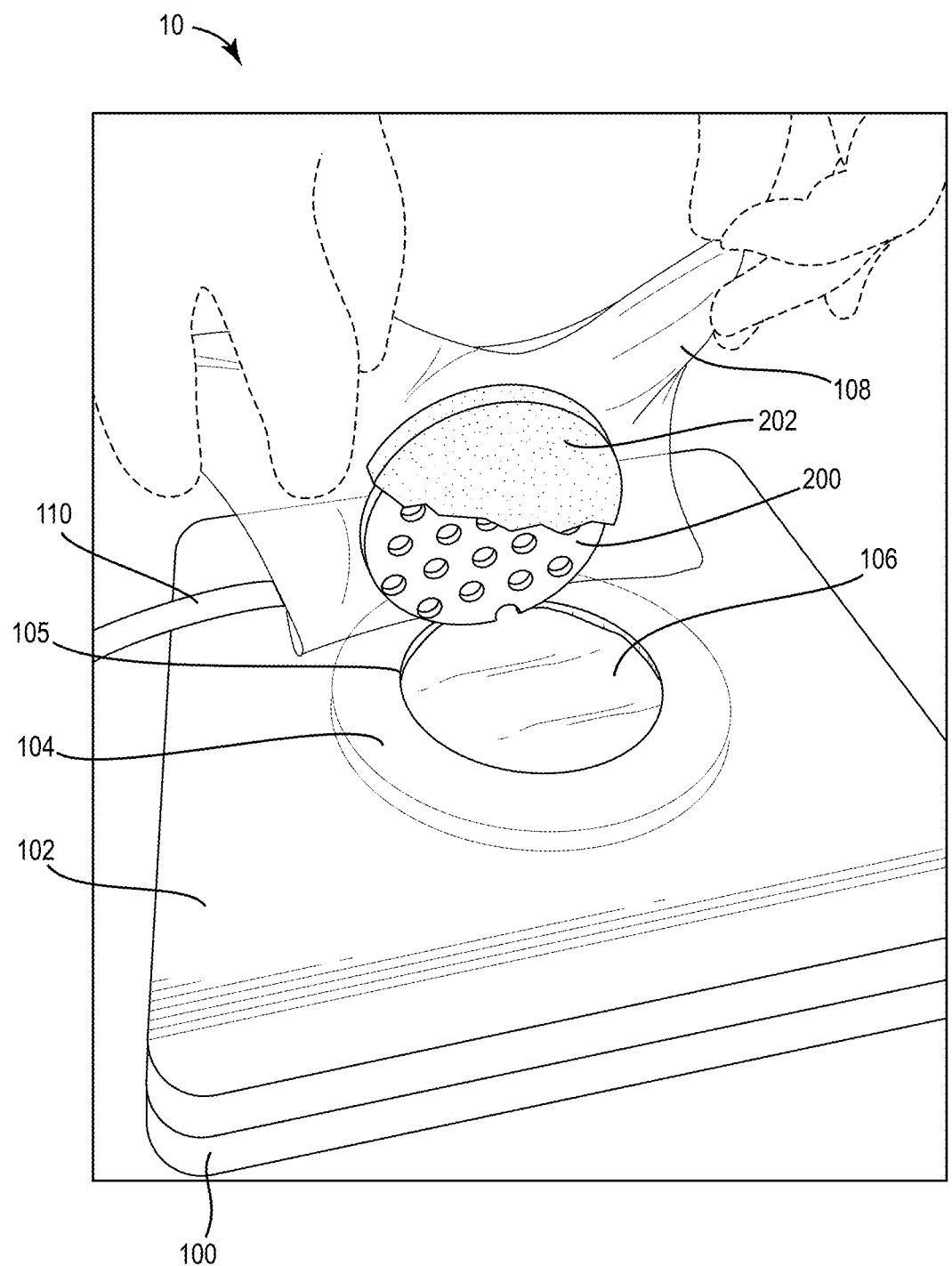
FIG. 11 illustrates a method of treatment wherein the device of the disclosure is used to model negative pressure and installation wound therapy.

Referring to FIGS. 9A and 11, in another embodiment, any of a variety of different dressing components and/or materials for use in a negative pressure therapy dressing may be used. And sized to fit in recess 104. For example, as depicted in FIGS. 9A and 11, foam manifolding layer 202 and perforated foam layer 200 may be used individually or in combination to illustrate the different responses from a simulated wound bed represented by conformable polymer 106. For example, perforated layer 200 may be used when debridement of the wound bed is desired. FIG. 9B illustrates an embodiment where a dressing is applied until about three centimeters from outer circumferential border 140 of base 104 (corresponding to the simulated periwound region).

Figure 10:
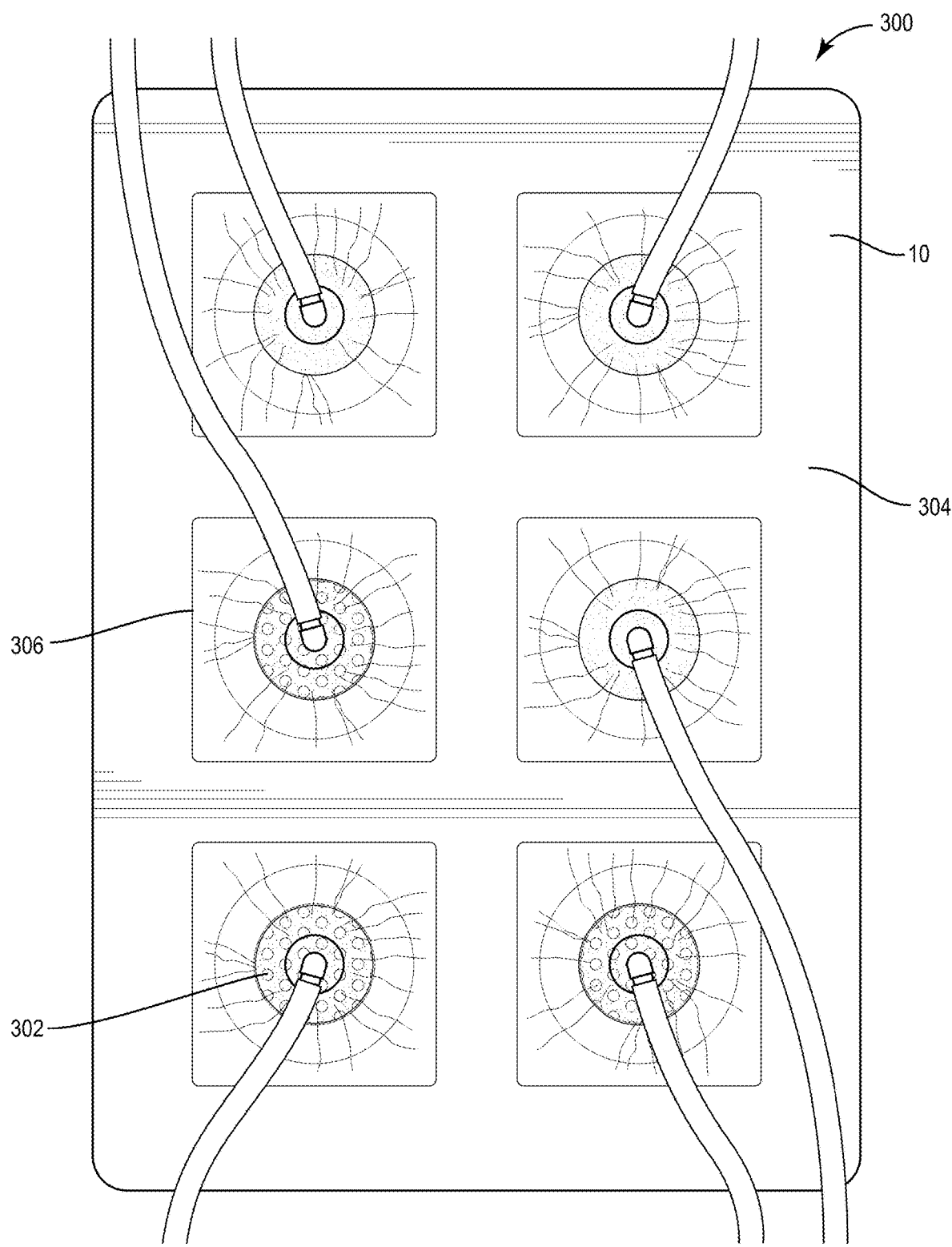
FIG. 10 depicts a top view of a wound training system where devices are aligned in parallel or in series.

A wound therapy training system is also disclosed. Referring to FIG. 10, wound therapy training system 300 may consist of a plurality of device 10 arranged or aligned to demonstrate multiple wound treatment sites 302. In some embodiments, the plurality of device 10 may be aligned in series 304 or in parallel 306.

A method of simulating negative pressure wound therapy is also provided. In one embodiment of the method, modular device 10 is assembled and negative pressure source 110 is activated. FIG. 11 shows a user in the process of assembling modular device 10, with support tray 100, elastic insert 102, base 104 within elastic insert 102, recess 105 within base 104, conformable polymer 106, dressing 108, and negative pressure source 110. The method allows a user to recreate a variety of treatment conditions and different types of common treatments encountered by clinicians and other health professionals.

The method may demonstrate wounds on a continuum. For example, the method can demonstrate, among other common wound therapy stages: non-viable tissue, slough in a wound bed, wounds requiring debridement, and wounds requiring granulation. The method may be used with multiple experiment conditions. One exemplary experiment condition includes about 1 cycle with about a 10-minute soak and about 30 minutes of negative pressure wound therapy at about 125 mmHg. Another exemplary experiment includes about 10 cycles with about a 20-minute soak and about 45 minutes of negative pressure wound therapy at about 125 mmHg. Yet another exemplary experiment includes about 8 cycles with about a 10-minute soak and 3.5 hours of negative pressure wound therapy at 125 mmHg.

Figure 12:
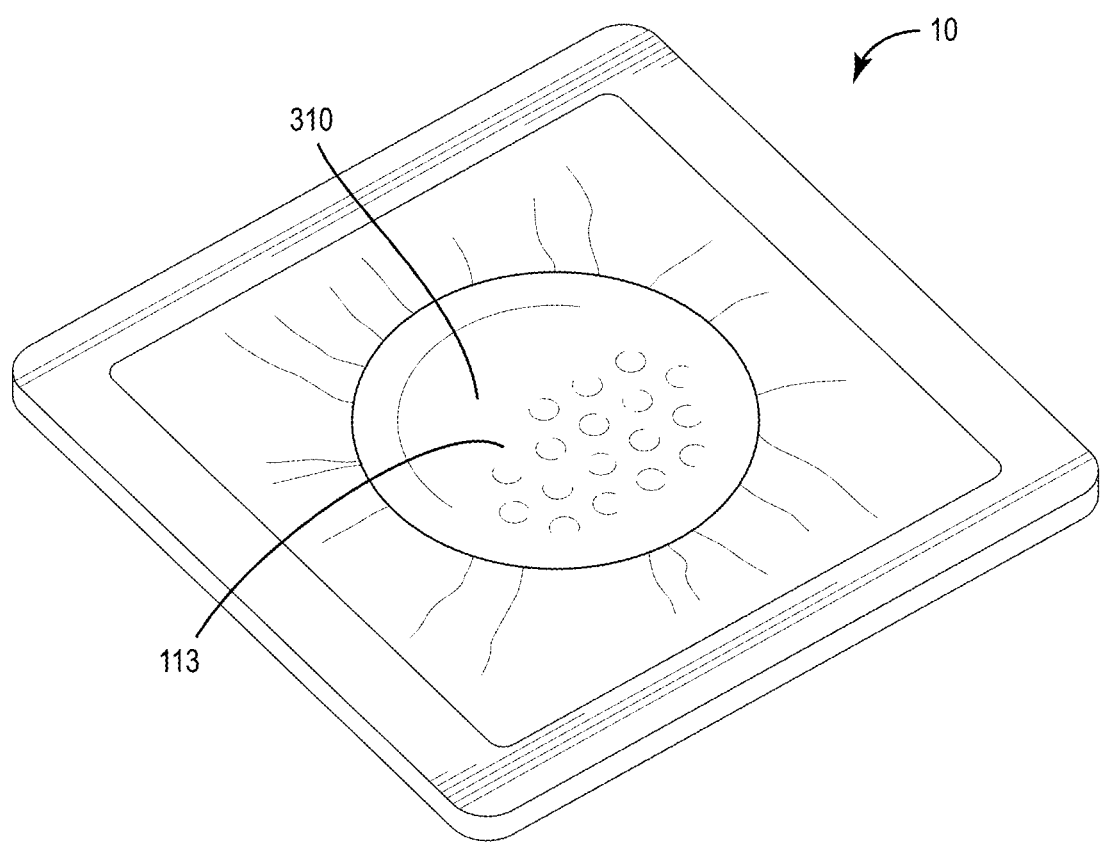
FIG. 12 illustrates a real-time visualization of a simulated wound bed undergoing negative pressure wound therapy treatment.

FIG. 12 shows a real-time visualization of wound bed 113 deforming from the underside of device 10. In some embodiments, due to the transparent nature of device 10, a real-time visualization of wound bed 113 deformation may be witnessed from any side or angle of device 10. The method of FIG. 11 and FIG. 12 also may be used to observe macrostrain 310 in simulated wound bed 113.

In some embodiments, the training aid could be used in a simulation lab to provide more in-depth training on various applications of the V.A.C. ULTA™ System and its therapy settings in more realistic scenarios, including, but not limited to, wounds that require debridement or those that only require granulation. Use in such a manner is intended to couple actual patient therapy devices with the simulated wound so that real time status feedback to the trainee on issues such as dressing leakage, fluid tube blockage, and any other indicators or alarms that may be relevant to the particular dressing type. The device and method can simulate a desired, normal healing trajectory for wounds that are progressing to closure as well as wounds that regress or fail to response and need alternative therapy options. For instance, the device can simulate an increase in common signs of an infected wound (redness and heat) and demonstrate the impact of potential treatment alterations and strategies to mitigate and manage therapy states, including pressure monitoring at the wound bed and screens to display the readings. It may be particularly useful in describing dynamic pressure control (DPC) and its effects on modulating applied negative pressure to the wound bed. Furthermore, a port in the base may be included to deliver a fluid to the wound bed to simulate exudate. Alternatively, the base may include small openings or perforations that would permit a fluid to be drawn into recess 105 under negative pressure to simulate development of exudate from the wound bed.

While various illustrative embodiments of the invention are described above, it will be apparent to one skilled in the art that various changes and modifications may be made therein without departing from the invention. The appended claims are intended to cover all such changes and modifications that fall within the true scope of the invention.

We claim:

1. A modular wound therapy training device comprising:
   a support tray;
   an elastic insert sized to fit within the tray, wherein the insert further comprises a base;
   a recess configured to simulate a wound bed and formed within the base;
   one or more simulated wound bed inserts configured to fit within the recess;

a dressing configured to be adhered on the elastic insert and over the base; and a negative pressure source configured to be coupled to the dressing.

2. The device of claim 1, wherein the elastic insert comprises a transparent rubber material.

3. The device of claim 1, wherein the wound bed insert comprises dermasol.

4. The device of claim 1, wherein the wound bed insert comprises pectin.

5. The device of claim 1, wherein the wound bed insert comprises collagen and dehydrated plasma proteins integrated into a woven viscous form.

6. The device of claim 1, wherein the wound bed insert comprises a cellulose membrane.

7. The device of claim 1, wherein the wound bed insert comprises a hydrocolloid.

8. The device of claim 7, wherein the wound bed insert further comprises a plurality of hydrocolloid strips.

9. The device of claim 1, wherein the wound bed insert includes an image of a wound on at least one surface of a conformable polymer.

10. The device of claim 1, wherein the tray comprises borders colored to depict a patient's skin.

11. The device of claim 1, further comprising water circulation passages within the device configured to receive water to maintain a desired temperature.

12. The device of claim 1, wherein the base further comprises a contour to simulate a contoured anatomy.

13. The device of claim 12, wherein the contour simulates an intergluteal cleft.

14. The device of claim 1, wherein the device is operatively coupled to one or more sensors.

15. The device of claim 14, wherein the one or more sensors supply readings to a software program indicating pressure levels of a treatment site.

16. The device of claim 14, wherein a plurality of force sensors are distributed in an array around the insert to determine applied force.

17. The device of claim 1, further comprising a peristaltic pump, wherein the pump extrudes a liquid from within the base either in or around the wound bed.

18. The device of claim 1, further comprising a negative pressure cutout template with appropriate dimensions to serve as a reference cutout for users.

19. The device of claim 1, further comprising a heater in the base to represent body temperature or inflammation.

20. The device of claim 19, wherein the device displays redness to demonstrate the impact of a potential treatment.

21. The device of claim 1, wherein a clear dermasol object is packed between the insert and the tray to simulate tunneling wounds and undermined areas.

22. The device of claim 1, further comprising a plurality of conformable polymers sized to fit in the recess.

23. The device of claim 22, wherein more than one conformable polymer may fit in one recess.

24. The device of claim 1, wherein the dressing is applied three centimeters from an outer circumferential border of the base.

25. A method of simulating negative pressure wound therapy, comprising:

placing one or more simulated wound bed inserts into a recess formed within a base, the recess configured to simulate a wound bed;

placing a dressing over the wound bed and adhered to the base; and applying a negative pressure to the dressing.

26. The method of claim 25, wherein the wound bed inserts demonstrate treatment of wounds on a continuum comprising wounds with non-viable tissue, slough in a wound bed, wounds requiring debridement, and wounds requiring granulation.

27. The method of claim 25, wherein the step of applying negative pressure comprises 1 cycle with a 10-minute soak and 30 minutes of negative pressure wound therapy at 125 mmHg.

28. The method of claim 25, wherein the step of applying negative pressure comprises 10 cycles with a 20-minute soak and 45 minutes of negative pressure wound therapy at 125 mmHg.

29. The method of claim 25, wherein the step of applying negative pressure comprises 8 cycles with a 10-minute soak and 3.5 hours of negative pressure wound therapy at 125 mmHg.

30. The method of claim 25, further comprising creating a real-time visualization of deformation of the wound bed by viewing any side of the base.

\* \* \* \* \*